US008941008B2

(12) United States Patent
Segawa et al.

(10) Patent No.: US 8,941,008 B2
(45) Date of Patent: Jan. 27, 2015

(54) DYE FOR PHOTOELECTRIC CONVERSION DEVICE, AND PHOTOELECTRIC CONVERSION FILM, ELECTRODE, AND SOLAR CELL USING SAME

(75) Inventors: Hiroshi Segawa, Chiba (JP); Takumi Kinoshita, Toyko (JP); Jun-ichi Fujisawa, Toyko (JP); Jotaro Nakazaki, Tokyo (JP); Satoshi Uchida, Miyagi (JP); Takaya Kubo, Kanagawa (JP)

(73) Assignees: The University of Tokyo, Tokyo (JP); Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 14/003,056

(22) PCT Filed: Mar. 6, 2012

(86) PCT No.: PCT/JP2012/055639
§ 371 (c)(1),
(2), (4) Date: Nov. 13, 2013

(87) PCT Pub. No.: WO2012/121236
PCT Pub. Date: Sep. 13, 2012

(65) Prior Publication Data
US 2014/0083491 A1   Mar. 27, 2014

(30) Foreign Application Priority Data

Mar. 7, 2011   (JP) ................................ 2011-048769

(51) Int. Cl.
| | | |
|---|---|---|
| H01L 31/04 | (2014.01) | |
| H01L 51/50 | (2006.01) | |
| C07F 15/00 | (2006.01) | |
| H01G 9/20 | (2006.01) | |
| C09B 57/10 | (2006.01) | |
| H01L 51/00 | (2006.01) | |
| H01L 31/0725 | (2012.01) | |
| H01L 51/42 | (2006.01) | |

(52) U.S. Cl.
CPC .......... *H01G 9/2004* (2013.01); *C07F 15/0053* (2013.01); *C09B 57/10* (2013.01); *H01G 9/2056* (2013.01); *H01L 51/0086* (2013.01); *H01L 31/0725* (2013.01); *H01L 51/422* (2013.01); *H01G 9/2031* (2013.01); *Y02E 10/542* (2013.01); *Y02E 10/549* (2013.01); *H01G 9/2013* (2013.01)
USPC ................................ 136/263; 313/504; 546/2

(58) Field of Classification Search
USPC ................... 546/2; 136/263, 252; 313/504
See application file for complete search history.

(56) References Cited

U.S. PATENT DOCUMENTS 5,789,592 A     8/1998 Gratzel et al.
6,084,176 A *   7/2000 Shiratsuchi et al. .......... 136/263
2007/0059551 A1  3/2007 Yamazaki

FOREIGN PATENT DOCUMENTS

| JP | 10-504521 | 5/1998 |
| JP | 2000-268889 | 9/2000 |
| JP | 2001-236999 | 8/2001 |

OTHER PUBLICATIONS

O'Regan and M. Gratzel, "A Low-cost, High-efficiency Solar Cell based on Dye-sensitized Colloidal TiO₂ Films," Nature, 353 pp. 737-740, 1991.
S. Altobello et al., "Sensitization of Nanocrystalline TiO₂ with Black Absorbers Based on Os and Ru Polypyridine Complexes," J. Am. Chem. Soc., 2005, 127 No. 44, pp. 15342-15343.
R. Leising et al., "Synthesis and Characterization of (Nitro)ruthenium Complexes that Utilize Identical Trans-Positioned Tertiary Phosphine Ligands," Inorg. Chem., 1990, 29, 4569-4574.
P. Falaras et al., "Characterization by Resonance Raman Spectroscopy of Sol-gel TiO₂ films sensitized by Ru(PPH₃)₂(dcbipy)Cl₂ complex for solar cells application," Solar Energy Materials & Solar Cells, vol. 64 (2000) 167-184.
International Preliminary Report on Patentability from PCT/JP2012/055639, mailed on Sep. 19, 2013; along with an English translation.
International Search Report PCT/JP2012/055639, mailed on Jun. 12, 2012.
Sullivan et al., "Cis-Trans Isomerism in (trpy) (PPh₃) RuCl₂. Comparisons between the Chemical and Physical Properties of a Cis-Trans Isomeric Pair", Inorg. Chem., vol. 19 No. 5, pp. 1404-1407, May 1, 1980.
Gagliardo et al., "Synthesis, Crystal Structure, and Redox and Photophysical Properties of Novel Bisphosphinoaryl Ru$^{II}$-Terpyridine Complexes," *Organometallics*, vol. 23, pp. 5833-5840, 2004.
Nazeeruddin et al., "Engineering of Efficient Panchromatic Sensitizers for Nanocrystalline TiO₂-Based Solar Cells," *J. Am. Chem. Soc.*, vol. 123, pp. 1613-1624, Feb. 3, 2001.
Falaras et al., "Synthesis and characterization of dichloro (2,2'-bipyridyl-4,4'-dicarboxylate)bis(triphenylphosphine)ruthenium(II) for efficient photosensitization of titanium oxide", *New J. of Chem.*, pp. 557-558, Jan. 1, 1998.
Ershov et al., "Mixed-Ligand Ruthenium(II) Complexes as Structural Units of Polynuclear Systems", *Russian Journal of Coordination chemistry*, vol. 27, No. 10, pp. 726-728, Jan. 1, 2001.
Extended European Search Report of EP Patent Application No. 12755461.6, which is dated Jul. 29, 2014.

* cited by examiner

Primary Examiner — Charanjit Aulakh
(74) Attorney, Agent, or Firm — Greenblum & Bernstein P.L.C.

(57) ABSTRACT

A photoelectric-conversion-device dye comprising a ruthenium metal complex, which includes a molecule including elemental phosphorous and the molecule forms a coordinate bond at least at the phosphorous atom, and which also includes a terpyridine derivative that forms a coordinate bond and has at least one adsorbing group that exhibits adsorptivity toward a metal oxide. The adsorbing group is selected from the group consisting of a carboxylic acid group, an ester thereof, or a salt thereof; a phosphonic acid group, an ester thereof, or a salt thereof; a hydroxyl group; an alkoxy group; and a sulfonic acid group or salt thereof. The dye exhibits absorption over a wide range from the visible light region to the near-infrared region, and as a result, a photoelectric conversion film, an electrode, and a solar cell having improved photoelectric conversion efficiency are provided.

17 Claims, 7 Drawing Sheets

The molecule structure of the dye used in Example

The absorption spectrum of the dye used in Example

The absorption spectrum of the dye used in Example

The IPCE spectrum of the solar cell fabricated in Examples and Comparative Examples

The IPCE spectrum of the solar cell fabricated in Examples and Comparative Examples

The IPCE spectrum of the solar cell fabricated in Examples and Comparative Examples

DYE FOR PHOTOELECTRIC CONVERSION DEVICE, AND PHOTOELECTRIC CONVERSION FILM, ELECTRODE, AND SOLAR CELL USING SAME

TECHNICAL FIELD

The present invention relates to a dye for a photoelectric conversion device, which is effective in photovoltaic applications such as solar cells or the like, and to a photoelectric conversion film, an electrode, and a solar cell employing the dye.

BACKGROUND ART

Because organic solar cells do not require frequent use of high-vacuum or high-temperature processing when fabricating them and, and low-cost raw materials can be used, there is an interest in organic solar cells as next-generation low-cost solar cells. There is particularly high interest in the Grätzel-type dye-sensitized solar cell.

The Grätzel-type dye-sensitized solar cell (see Non-Patent Citation 1) has a structure that includes a photoelectric conversion electrode in which a dye is adsorbed on a metal nanoparticle layer of titanium oxide or the like that is sintered on a transparent conductive substrate, a counter electrode formed of a conductive substrate that has a thin film of Pt or a carbon material formed thereon, and an electrolyte layer including a redox couple such as iodine that is sandwiched between these electrodes. The photoelectric conversion efficiency of this dye-sensitized solar cell greatly depends on the solar absorption capability of the dye. Although the reported value for the Grätzel-type dye-sensitized solar cell is 11% (1-cm square in size), which is the highest reported photoelectric conversion efficiency among the organic solar cells, the photoelectric conversion efficiency needs to be further enhanced in order to achieve practical use. Up to now, there has been research and development of long-wavelength absorbing dyes, and a representative dye is N719 dye, or Black Dye, which is one of the Ru metal polypyridine complexes. Even with the Black Dye used in the dye-sensitized solar cell exhibiting the highest conversion efficiency at the present time, the absorption edge is at about 900 nm, and it is necessary to shift the absorption edge further toward longer wavelengths. Under such circumstances, a complex that includes Os metal and a pyridine derivative, serving as a ligand, and that allows for a greater long-wavelength shift than the Black Dye has been investigated. When a pyridine derivative that serves as a ligand is appropriately selected, the absorption-edge wavelength of an OS dye shifts. With a dye-sensitized solar cell fabricated by using a dye in which substituents (X) of a ligand are assumed to be H, COOH, and $C(CH_3)_3$, its IPCE (Incident Photon-to-current Conversion Efficiency) starts to increase near 1100 nm and reaches about 30 to 50% at 900 nm; however, at 800 nm, the IPCE is about 50% at most (see Non-Patent Citation 2). In order to achieve high photoelectric conversion efficiency, it is essential to achieve high IPCE values in all wavelength regions, including the near-infrared region, the visible light region, and the ultraviolet region.

In addition, in the past, there has been various research on Ru complexes, including their absorption characteristics and so forth, and, although research into the absorption characteristics of, for example, Ru complexes having terpyridine and a phosphine derivative as ligands has also been carried out, absorption was not exhibited over the entire visible light region (for example, Non-Patent Citation 3).

In addition, Patent Citation 1 discloses a metal complex in which coordinate bonds are formed involving two terpyridine molecules having phosphonic acid or carboxylic acid (complex given by Expression (8) in Patent Citation 1), a metal complex in which coordinate bonds are formed involving one terpyridine molecule having phosphonic acid and a predetermined bidentate or tridentate aza ligand (complex given by Expression (9) in Patent Citation 1), and a metal complex in which coordinate bonds are formed involving bipyridine having phosphonic acid, a predetermined bidentate or tridentate aza ligand, and a predetermined monodentate ligand (complex given by Expression (10) in Patent Citation 1). However, there is no description of a metal complex in which coordinate bonds are formed involving terpyridine having phosphonic acid or carboxylic acid and a phosphorus-based ligand.

CITATION LIST

Patent Citations

Patent Citation 1: JP-A-1998-504521

Non-Patent Citations

Non-Patent Citation 1: Nature, 1991, 353, p. 737, O'Regan and M. Gratzel.

Non-Patent Citation 2: J. Am. Chem. Soc., 2005, 127, p. 15324, S. Sltobello, R. Argazzi, S. Caramori, C. Contado, S. Da Fre, P. Rubino, C Chone, G. Larramona, and C. A. Bignozzi.

[Non-Patent Citation 3] Inorg. Chem., 1990, 29, p. 4569-4574, Randolph A. Leising, Stephen A. Kubow, and Kenneth J. Takeuchi.

DISCLOSURE OF INVENTION

Technical Problem

The present invention has been conceived in light of the above-described current circumstances, and an object thereof is to provide a dye for a photoelectric conversion device, which exhibits absorption over a wide range from the visible light region to the near-infrared region.

An additional object of the present invention is to provide a photoelectric conversion film, an electrode, and a solar cell having improved photoelectric conversion efficiency.

Solution to Problem

In order to solve the above-described problems, the present inventors have performed various investigations, and, as a result, have gained the insights that a complex that exhibits an absorption peak due to a spin-forbidden transition is included among the Ru complexes, that the Ru complex having such a characteristic exhibits absorption over the entire range from the visible light region to the near-infrared region (300 to 1000 nm), and that it is possible to considerably improve the photoelectric conversion efficiency by employing this complex as a dye for a photoelectric conversion device, and thus, the present invention has been achieved based on these insights.

In other words, solutions to the above-described problems are as described below.

[1] A photoelectric-conversion-device dye comprising:

at least one type of metal complex in which a molecule including elemental phosphorus is included and the molecule also forms a coordinate bond at least at the phosphorus atom, and in which the coordinate bond is formed involving a terpyridine derivative having at least one adsorbing group that exhibits adsorptivity toward a metal oxide.

[2] A photoelectric-conversion-device dye according to [1], wherein the metal complex is a metal complex that exhibits absorption due to a spin-forbidden transition.

[3] A photoelectric-conversion-device dye according to [1] or [2], wherein the metal complex is represented by Expression (I) below:

$$[Ru(L^1)(L^2)_n(L^3)_{3-n}] \quad (I)$$

where $L^1$ indicates a terpyridine derivative represented by Expression (L1) below; $L^2$ represents an organic molecule including elemental phosphorus, represented by Expression (L2) below; $L^3$ indicates a halogen atom, NCS$^-$, SCN$^-$, CN or NCO$^-$; and n is an integer of 1 to 3;

[Ch. 1]

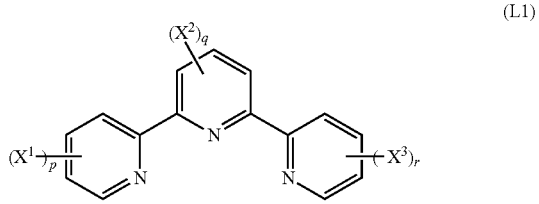

(L1)

where $X^1$ to $X^3$ represent adsorbing groups that are the same as or different from each other and that have adsorptivity toward a metal oxide; and, although p, q, and r are each an integer of 0 to 5, at least one of them is equal to or greater than 1; and $$P(R^1)(R^2)(R^3) \quad (L2)$$

where $R^1$ to $R^3$ each represent an alkyl group, an alkenyl group, an aryl group, an alkyloxy group, or an aryloxy group that are the same as or different from each other; $R^1$ to $R^3$ may have a substituent; and $R^1$ to $R^3$ may also be bonded with each other to form one or more rings if possible.

[4] A photoelectric-conversion-device dye according to any one of [1] to [3], wherein the adsorbing group is a carboxylic acid group (—COOH), a salt thereof, or an ester thereof.

[5] A photoelectric-conversion-device dye according to [3] or [4], wherein $L^2$ is an organic molecule including elemental phosphorus, represented by (L2-1) or (L2-2) below:

[Ch. 2]

$$P(OR^{11})_m(R^{12})_{3-m} \quad (L2-1)$$

(L2-2)

where, in these Expressions, $R^{11}$ and $R^{12}$ each represent an alkyl group or an aryl group, which may include substitution; m is an integer of 0 to 3; when a plurality of $OR^{11}$ and $R^{12}$ are included, they may be the same as or different from each other; Cy represents a ring group having one phosphorus atom and two oxygen atoms as constituent atoms of the ring; Cy may have a substituent if possible; Cy may also take a condensed form including one or more rings; $R^{21}$ represents an alkyl group, an aryl group, an alkyloxy group, or an aryloxy group; $R^{21}$ may have a substituent; and $R^{21}$ may form a ring, if possible, by bonding with a constituent atom of the ring in Cy.

[6] A photoelectric-conversion-device dye according to any one of [1] to [5], wherein n is 1.

[7] A photoelectric conversion film at least comprising:
a photoelectric-conversion-device dye according to any one of [1] to [6]; and
a metal oxide semiconductor.

[8] An electrode comprising:
a photoelectric conversion film according to [7].

[9] A solar cell at least comprising:
an electrode according to [8];
a counter electrode therefor; and
an electrolyte layer that is disposed therebetween.

[10] A solar cell according to [9], wherein the electrolyte layer contains at least a pyridine derivative.

[11] A tandem-type solar cell at least comprising:
a solar cell according to [9] or [10].

Advantageous Effects of Invention

The present invention can provide a dye for a photoelectric conversion device, which exhibits absorption over a wide range from the visible light region to the near-infrared region.

In addition, the present invention can provide a photoelectric conversion film, an electrode, and a solar cell having improved photoelectric conversion efficiency.

BEST MODE FOR CARRYING OUT THE INVENTION

Figure 1:
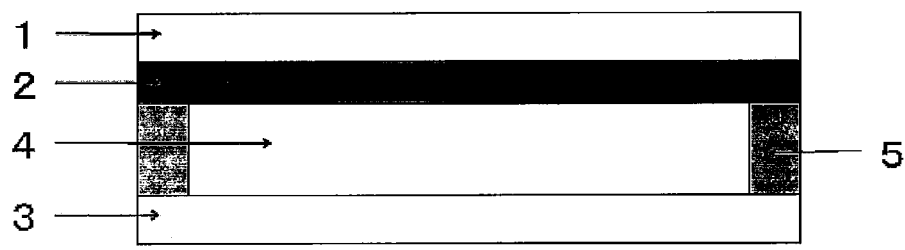
FIG. 1 is a schematic cross-sectional view of an example solar cell according to the present invention.

The present invention will be described in detail below.

1. Dye for Photoelectric Conversion Device

The present invention relates to a dye for a photoelectric conversion device, which includes at least one type of metal complex in which a molecule that includes elemental phosphorus is included, and the molecule also forms a coordinate bond at least at this phosphorus atom, and in which a coordinate bond is formed involving a terpyridine derivative having at least one adsorbing group that exhibits adsorptivity toward metal oxides. A metal complex in which a terpyridine derivative having an adsorbing group and a molecule including elemental phosphorus form a coordinate bond at the elemental phosphorus (for example, an Ru complex) exhibits an absorption characteristic that is shifted toward long wavelengths, and exhibits relatively high absorption near the wavelength of 800 nm. Because the complex exhibits absorption over the entire visible light region, ranging from short wavelengths to long wavelengths, as well as in the near-infrared region, it possesses an excellent light-sensitization effect. Therefore, by employing the metal complex of the present invention as a light-sensitized dye for photoelectric conversion, it is possible to improve the photoelectric conversion efficiency. Because the metal complex according to the present invention has the ligands of predetermined combinations described above, the metal complex exhibits a spin-forbidden transition due to a spin-orbit interaction, and exhibits absorption originating therefrom in the range from the long-wavelength visible light region to the near-infrared region (for example, 600 to 1000 nm). With regard to the absorption characteristics due to the spin-forbidden transition, it is possible to confirm that the difference between the absorption wavelength and the emission wavelength is small by means of time-resolved emission analysis, time-dependent density functional theory (TD-DFT), and so forth.

It is preferable that the central metal of the above-described metal complex be Ru. Ru(II) is particularly preferable.

The above-described metal complex has a terpyridine derivative as a ligand. This terpyridine derivative has an adsorbing group that can be adsorbed to a metal oxide semiconductor (for example, $TiO_2$). The adsorbing group is exemplified by a carboxylic acid group, an ester thereof, and a salt thereof (—COOY); a phosphonic acid group, an ester thereof, and a salt thereof (—PO(OY)$_2$); a hydroxy group and an alkyloxy group (—OY); and a sulfonic acid group and a salt thereof. Here, Y in each case represents, a hydrogen atom, an alkyl group (preferably, an alkyl group of $C_{1-30}$, $C_{1-20}$, $C_{1-10}$, $C_{1-5}$), or a cation (for example, an alkaline metal cation, an alkaline earth metal cation, an ammonium, and so forth). It is particularly preferable that the adsorbing group be a carboxylic acid group, an ester thereof, or a salt thereof (—COOY).

The above-described terpyridine has at least one adsorbing group. It is preferable that three pyridine rings in the terpyridine each have one adsorbing group. Although there is no particular limitation about the substitution position of the adsorbing group, it is preferable that the substitution be at the 4-position with respect to nitrogen in the 1-position.

The above-described terpyridine derivative is an example of the terpyridine derivative represented by Expression (L1) below.

[Ch. 3]

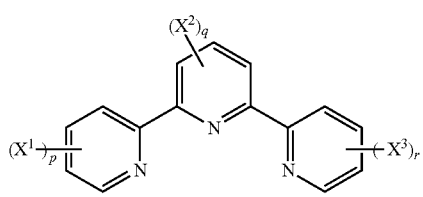

(L1)

$X^1$ to $X^3$ are the same as or different from each other, representing adsorbing groups that exhibit adsorptivity toward metal oxides; although p, q, and r are each an integer of 0 to 5, at least one of them is equal to or greater than 1.

Preferable examples of $X^1$ to $X^3$ are the same as those described above, and it is particularly preferable that $X^1$ to $X^3$ be a carboxylic acid group, an ester thereof, or a salt thereof (—COOY).

In addition, it is preferable that p, q, and r all be 1, and it is preferable that $X^1$ to $X^3$ be respectively bonded to the carbon atom at the 4-position in each pyridine ring.

The above-described metal complex has a molecule that includes elemental phosphorus as a ligand. It is preferable that the molecule be an organic molecule having elemental phosphorus. This organic molecule forms a coordinate bond with a metal at least at the elemental phosphorus. Molecules represented by Expression (L2) below are examples of the organic molecule including elemental phosphorus described above.

$P(R^1)(R^2)(R^3)$ (L2)

$R^1$ to $R^3$ are the same as or different from each other, representing an alkyl group, an alkenyl group, an aryl group, an alkyloxy group, or an aryloxy group, and these may include substituents, which may also be bonded with each other to form one or more rings if possible.

The alkyl groups represented by each of $R^1$ to $R^3$ may be straights chain or branched chains. The alkyl group is preferably $C_{1-30}$, more preferably, $C_{1-20}$, yet more preferably, or, even more preferably, $C_{1-5}$. This is the same for the alkyl group in the alkyloxy groups represented by each of $R^1$ to $R^3$.

The alkenyl groups represented by each of $R^1$ to $R^3$ are preferably $C_{2-30}$, more preferably, $C_{2-20}$, yet more preferably, $C_{2-10}$, or, even more preferably, $C_{2-5}$.

The aryl groups represented by each of $R^1$ to $R^3$ may be of a single-ring structure or of a condensed ring structure including two or more rings. In addition, the aryl group may also be a hydrocarbon-based aryl group such as a phenyl group or the like, or a heteroaryl group such as a thienyl group or the like. This is the same for the aryl group in an aryloxy group represented by each of $R^1$ to $R^3$.

The light-sensitization effect tends to be greater when at least one of $R^1$ to $R^3$ is an alkyloxy group or an aryloxy group.

These groups may have one or more substituents if possible. These is no particular limitation on the substituent so long as the absorption characteristic of the metal complex is not deteriorated. Such groups are exemplified by an alkyl group, an alkyloxy group, an alkylthio group, a dialkylamino group, a trialkylsilyl group, an alkyloxyalkyl group, an alkyloxycarbonyl group, and an alkyl halide group that may be a straight chain or a branched chain; as well as an aryl group, an aryloxy group, an arylthio group, a diarylamino group, an aryloxyalkyl group, a halogen, a cyano group, a hydroxyl group, a nitro group, an amino group, a mercapto group, an amide group, a carboxyl group, a formyl group, an acyl group, a sulfo group, a phosphoryl group, and so forth, including a phenyl group, a thienyl group, or the like which may have an additional substituent or may have a condensed ring structure including two or more rings.

In addition, in Expression (L2) described above, $R^1$ to $R^3$ may be bonded with each other to form one or more rings if possible. It is preferable that the ring to be formed be a five- or six-member ring. Also, $R^1$ to $R^3$ may be bonded to form a bridged-ring structure. The ring to be formed may have a substituent such as an alkyl group or the like, or the ring to be formed may take the form of condensed rings having aliphatic rings or aryl rings.

Organophosphorus compounds represented by Expression (L2-1) or (L2-2) below are examples of the above-described organic molecules including elemental phosphorus.

[Ch. 4]

$P(OR^{11})_m(R^{12})_{3-m}$ (L2-1)

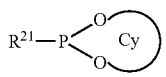
(L2-2)

In these Expressions, $R^{11}$ and $R^{12}$ each represent an alkyl group or an aryl group, which may include substitution; m is an integer of 0 to 3; when a plurality of $OR^{11}$ and $R^{12}$ are included, they may be the same as or different from each other; Cy represents a ring group having one phosphorus atom and two oxygen atoms as constituent atoms of the ring; Cy may have a substituent if possible; Cy may also take a condensed form including one or more rings; $R^{21}$ represents an alkyl group, an aryl group, an alkyloxy group, or an aryloxy group; $R^{21}$ may have a substituent; and $R^{21}$ may form a ring if possible, by bonding with a constituent atom of the ring in Cy.

An alkyl group and an aryl group represented by each of $R^{11}$ and $R^{12}$, as well as an alkyl group, an aryl group, an alkyloxy group, and an aryloxy group represented by $R^{21}$, are the same as the individual groups represented by each of $R^1$ to $R^3$, and the preferable conditions are also the same.

In addition, $R^{11}$, $R^{12}$, $R^{21}$, and Cy may have one or more substituents, examples of which include the same substituents as those described above.

In addition, Cy may take a condensed form together with one or more aryl rings, such as a benzene ring or the like, or one or more aliphatic rings, such as a cyclohexane ring or the like.

Also, the light-sensitization effect tends to be greater when m is equal to or greater than 1 in Expression (L2-1).

Although the following compounds are included in examples of the ligand that includes elemental phosphorus in the metal complex according to the present invention, there is no limitation thereto. Note that, in the following Expressions, Q indicates a hydrogen atom or an alkyl group of $C_{1-20}$ in a straight chain or a branched chain; a, b, and c indicate integers of 1 to 3 that are the same as or different from each other; and R indicates a hydrogen atom or a substituent.

[Ch. 5]

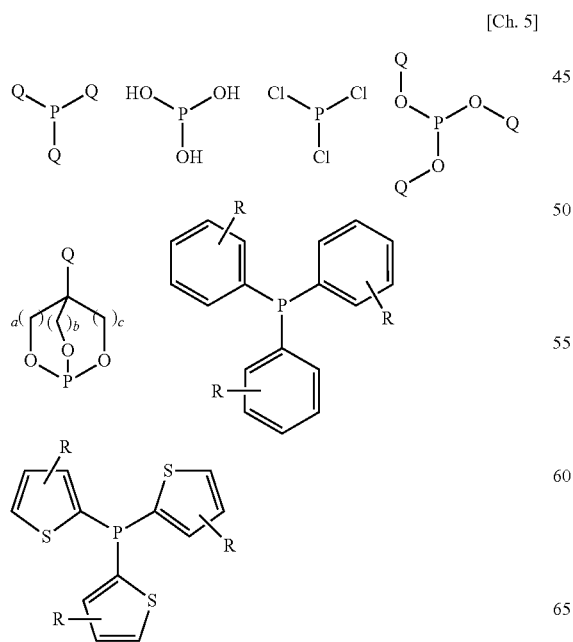

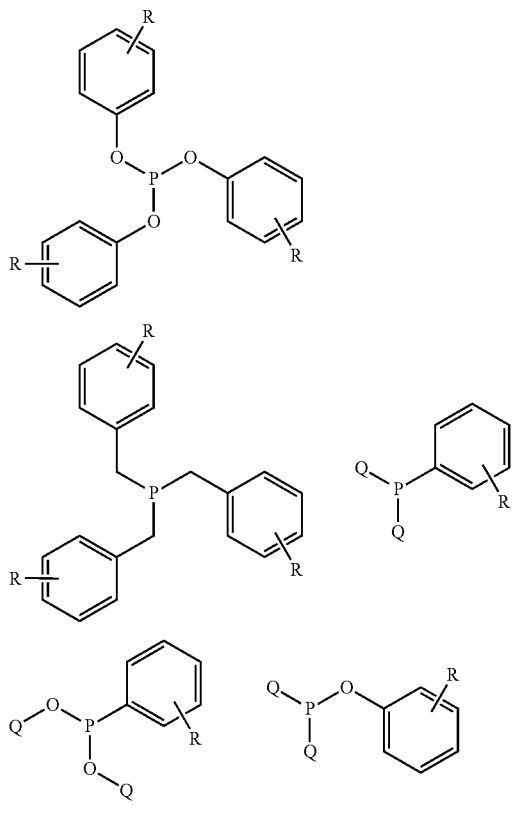

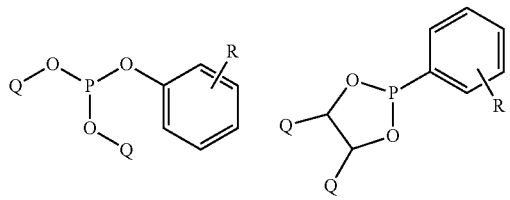

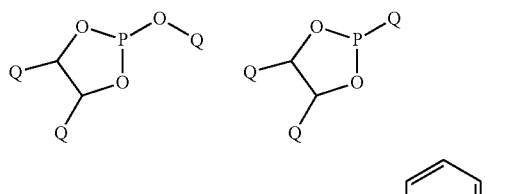

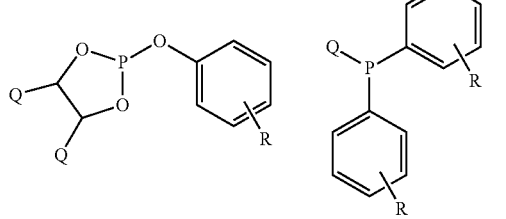

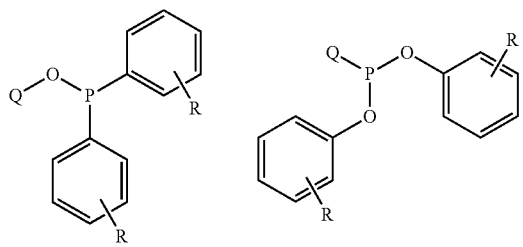

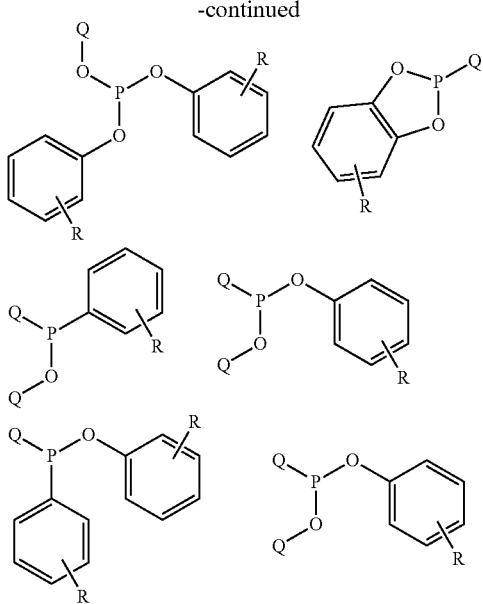

The above-described metal complex according to the present invention may have an additional ligand and/or anions other than the above-described ligands. Preferable examples of the additional ligand and/or anions include a halogen anion, NCS⁻, SCN⁻, CN, and NCO⁻.

Preferable examples of the above-described metal complex according to the present invention include Ru complexes represented by Expression (I) below.

$$[Ru(L^1)(L^2)_n(L^3)_{3-n}] \qquad (I)$$

$L^1$ indicates a terpyridine derivative represented by Expression (L1) below; $L^2$ represents an organic molecule including elemental phosphorus represented by Expression (L2) below; $L^3$ indicates a halogen anion (for example, Cl⁻, Br⁻, I⁻), NCS⁻, SCN⁻, CN or NCO⁻; and n is an integer of 1 to 3. However, when a plurality of $L^2$ and $L^3$ are respectively included in Expression, the plurality of $L^2$ and $L^3$ may respectively be the same as or different from each other.

[Ch. 6]

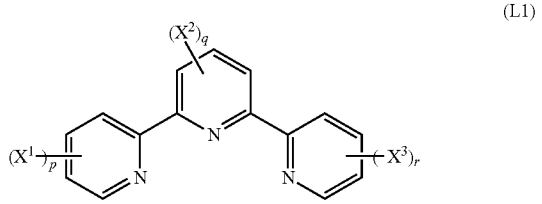

(L1)

$X^1$ to $X^3$ represent adsorbing groups that are the same as or different from each other and that have adsorptivity toward a metal oxide; and, although p, q, and r are each an integer of 0 to 5, at least one of them is equal to or greater than 1.

$$P(R^1)(R^2)(R^3) \qquad (L2)$$

$R^1$ to $R^3$ each represent an alkyl group, an alkenyl group, an aryl group, an alkyloxy group, or an aryloxy group that are the same as or different from each other; $R^1$ to $R^3$ may have a substituent; and $R^1$ to $R^3$ may also be bonded with each other to form one or more rings if possible.

The meaning of the individual symbols in Expressions (L1) and (L2), as well as their preferable conditions, are the same as those described above. In addition, it is preferable that $L^2$ be the organic molecule including elemental phosphorus represented by the above-described Expression (L2-1) or (L2-2).

In Expression (I), it is preferable that n be 1, specifically, that the Ru complex be one represented by Expression (II) below. The meanings of individual symbols in Expression (II) below are the same as those in Expression (I) and their preferable conditions are also the same.

[Ch. 7]

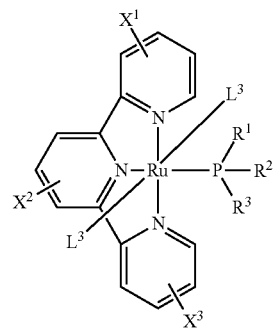

(II)

The Ru complex represented by the above-described Expression (I) can be fabricated by combining various methods by using, for example, commercially available reagents, and so forth. An example is given below. First, ruthenium trichloride and a terpyridine derivative are subjected to thermal reflux in an organic medium (for example, ethanol) under an atmosphere of inert gas (for example, argon gas), thus obtaining [Ru(II)(terpyridine derivative)(Cl)₃] as an intermediate. An organophosphorus compound such as phosphine or the like is added to the organic medium (for example, N,N-dimethylformamide) solution having this intermediate, in the presence of an amine such as ethylenediamine or the like, and thus, the Ru complex of Expression (I) can be fabricated by advancing the reaction.

The metal complex according to the present invention exhibits an absorption characteristic that is shifted toward long wavelengths, and exhibits relatively high absorption near the wavelength of 800 nm. Because the metal complex exhibits absorption over the visible light region ranging from short wavelengths to long wavelengths, as well as in the entire near-infrared region, it possesses an excellent light-sensitization effect. For example, with a terpyridine Ru complex disclosed in Non-Patent Citation 3 described above, the absorption-peak wavelength is at 636 nm at most, and, also based on this fact, it is clear that the Ru complex according to the present invention has an absorption characteristic that is shifted toward long wavelengths as compared with the conventional terpyridine Ru complex.

By employing the metal complex according to the present invention as a light-sensitized dye for photoelectric conversion, it is possible to improve the photoelectric-conversion rate. For example, as compared with the dye (Black Dye) exhibiting the highest photoelectric conversion efficiency of about 11% in dye-sensitized solar cells, with which photovoltaic current starts to be generated at a wavelength of about 900 nm, a dye-sensitized solar cell employing the dye of the present invention achieves a high IPCE value close to 80% over the entire visible light region starting from further on the long wavelength side (about 950 nm). Therefore, by employing the dye of the present invention, it is possible to increase the solar utilization rate beyond that achieved by the existing dyes, thus enabling high-efficiency photoelectric conversion.

2. Photoelectric Conversion Film and Electrode Having the Same

The present invention also relates to a photoelectric conversion film including at least the dye of the present invention, for a photoelectric conversion device and a metal oxide semiconductor, as well as to an electrode having the photoelectric conversion film. In the above-described photoelectric conversion film, it is preferable that the above-described dye for a photoelectric conversion device be adsorbed on a metal oxide semiconductor. Various methods can be used as the dye adsorption method for adsorbing the dye on a metal oxide semiconductor. An example is a method in which adsorption is achieved by immersing a semiconductor layer formed of a metal oxide semiconductor in a dye solution. Although there is no particular limitation on the amount of immersing time so long as adsorption is achieved so as to obtain sufficient photoelectric conversion characteristics, it is preferable that the immersing time be 1 to 30 hours, and it is particularly preferable that the immersing time be 5 to 25 hours. In addition, a medium or a substrate may be heated when immersing, as needed. In preparing a dye solution, it is preferable that the concentration thereof be 0.1 to 1000 mmol/L, and it is preferable that the concentration thereof be about 0.1 to 1 mmol/L.

There is no particular limitation on the medium to be used so long as the dye can be dissolved therein but the semiconductor layer does not dissolve therein, and media that can be used include alcohol, such as methanol, ethanol, 1-propanol, 2-propanol, 1-butanol, 2-butanol, t-butanol, and so forth; nitrile-based media, such as acetonitrile, propionitrile, methoxypropionitrile, glutaronitrile, and so forth; as well as benzene, toluene, o-xylene, m-xylene, p-xylene, pentane, heptane, hexane, cyclohexane, heptane, acetone, methyl ethyl ketone, diethyl ketone, 2-butanone, diethyl ether, tetrahydrofuran, ethylene carbonate, propylene carbonate, nitromethane, dimethylformamide, dimethyl sulfoxide, dimethoxyethane, γ-butyrolactone, γ-valerolactone, sulfolane, methoxyacetonitrile, dimethylacetamide, dioxolane, and so forth. In addition, it is also possible to use a plurality of media selected from these media in a mixture. In addition, it is possible to add a bile-acid derivative such as deoxycholic acid to the dye solution as an additive.

Although there is no particular limitation on the above-described metal oxide semiconductor, the metal oxide semiconductor is, for example, $SnO_2$, $TiO_2$, or ZnO, and multiple types thereof may be used in combination. $TiO_2$ and ZnO are particularly preferable.

As for methods of forming the semiconductor layer, the semiconductor layer can be obtained by coating a substrate with the above-described semiconductor in the form of a dispersed nanoparticle paste, sol colloidal solution, or the like by using a known method. The coating method in this case is not particularly limited, including a method of obtaining the semiconductor layer in the form of a thin film by using a casting method, a dip-coating method, a bar-coating method, in addition to various printing methods, including a screen printing method. Although the thickness of the semiconductor layer is arbitrary, it should be equal to or greater than 5 μm and equal to or less than 40 μm, and it is preferable that the thickness be equal to or greater than 10 μm and equal to or less than 25 μm.

An electrode for a solar cell or the like can be fabricated by forming the above-described photoelectric conversion film on a conductive substrate.

The conductive substrate is exemplified by substrates in which a conductive layer is formed on a non-conductive substrate, as well as substrates in which the substrates themselves possess conductivity. In addition, the material, thickness, size, shape, and so forth can appropriately be selected in accordance with the purpose. In addition to a metal such as gold, silver, copper, or the like, a glass plate or a polymer film that is non-conductive, colorless or colored, and light transmitting can be used as the substrate. Specifically, examples include films made of polyester such as polyethylene terephthalate, polyamide, polysulfone, polyethersulfone, polyether ether ketone, polyphenylene sulfide, polycabonate, polyimide, polymethyl methacrylate, polystyrene, cellulose triacetate, polymethylpentene, and so forth. Note that the substrate in the present invention has a smooth surface at room temperature, and the surface thereof may be flat or curved and may be deformed when subjected to stress. In addition, in order to impart conductivity to the substrate, for example, a metal thin film of gold, tungsten or the like or a conductive film formed of metal oxide may be disposed on the surface thereof. Metal oxides that can be suitably employed are, for example, Indium Tin Oxide (ITO($In_2O_3$:Sn)), Fluorine-doped Tin Oxide (FTO($SnO_2$:F)), Aluminum-doped Zinc Oxide (AZO(ZnO:Al)) or the like, in which a metal oxide of indium, tin, zinc or the like is doped with a trace amount of other metal elements.

The conductive film normally has a film thickness of 10 nm to 2 μm, preferably, 100 nm to 1 μm, and, in addition, the sheet resistance thereof normally is from 0.5 to 100 Ω/sq, preferably, from 2 to 50 Ω/sq. These conductive films can be fabricated on a substrate by using known methods such as, vacuum deposition, ion plating, CVD, electron beam vacuum deposition, sputtering, and so forth.

3. Solar Cell

The present invention also relates to a solar cell having the above-described electrode and to a so-called tandem-type solar cell unit in which this solar cell and a second solar cell are arrayed in series.

There is no particular limitation on the configuration of the solar cell of the present invention. Various general configurations of dye-sensitized solar cells can be employed. One example thereof is schematically shown in the cross-sectional view in FIG. 1. The solar cell shown in FIG. 1 includes an electrode having a photoelectric conversion film 2 on a light-transmitting conductive substrate 1, a counter electrode 3 thereof, and an electrolyte layer 4 that is disposed therebetween. The electrolyte layer 4 can be formed by loading electrolyte components in the form of liquid, solid, or the like into the space between the two electrodes and by sealing them with a sealing material 5.

There is no particular limitation on the electrolyte. It is preferable to use a liquid-based electrolyte. There is no particular limitation on the liquid-based electrolyte, and a liquid-based electrolyte normally includes, as basic components, a substance that exhibits reversible electrochemical oxidation-reduction property (which can be dissolved in the medium), and, additionally, a supporting electrolyte as needed.

Any medium can be used as the medium so long as it is a medium generally used in an electrochemical cell or a battery. Specifically, it is possible to use methanol, ethanol, tetrahydrofuran, propylene carbonate, nitromethane, acetonitrile, dimethylformamide, dimethyl sulfoxide, hexamethylphosphoramide, ethylene carbonate, dimethoxyethane, γ-butyrolactone, γ-valerolactone, sulfolane, dimethoxyethane, propionitrile, glutaronitrile, adiponitrile, methoxyacetonitrile, dimethylacetamide, methylpyrrolidinone, dioxolane, polyethylene glycol, and so forth.

In addition, although the substances exhibiting reversible electrochemical oxidation-reduction properties normally include so-called redox materials, there is no particular limitation on the types thereof. Such substances include, for example, a substance containing a metal iodine salt formed between $I_2$ and LiI, NaI, KI, or the like, a tetraalkylammonium iodine salt, such as tetraalkylammonium iodide or the like, or a quaternary imidazolium iodine salt; a substance containing a metal bromide formed between $Br_2$ and LiBr, NaBr, KBr, or the like, a tetraalkylammonium bromine salt, such as tetraalkylammonium bromide or the like, or a quaternary imidazolium bromine salt; and a substance in which a plurality of the above-described electrolyte components are mixed. Furthermore, as components other than those described above, it is possible to add a pyridine derivative, such as 4-t-butylpyridine or the like.

There is also no particular limitation on the counter electrode forming the above-described solar cell. It is possible to use conductive substrates that can be used for the above-described electrode of the present invention. In particular, those having a catalyst layer formed of Pt, carbon, or the like are preferable because movement of holes is improved.

The solar cell of the present invention may be used in combination with a second solar cell to form a tandem-type solar cell. An example thereof is a tandem-type solar cell formed by connecting the solar cell of the present invention in series with a second solar cell on the surface thereof that is irradiated with light. As the second solar cell in this example, it is preferable to employ a solar cell that exhibits a superior photoelectric conversion rate at a wavelength further on the short wavelength side (for example, a wavelength of 300 to 700 nm), as compared with the solar cell of the present invention. The second solar cell is not limited in any way with respect to the material thereof so long as a semiconductor layer for photoelectric conversion is included. The material may be an inorganic material such as silicon or the like, or it may be an organic material such as an organic semiconductor film, a dye-sensitized photoelectric conversion film, or the like. JP-A-2006-100047, JP-A-2006-32260, and WO2010/029961 include descriptions of tandem-type solar cells, and they may be referred to.

EXAMPLES

The present invention will specifically be described below by means of Examples; however, the present invention is not limited in any way by these Examples.

Example 1

Figure 2:
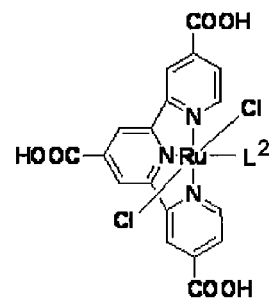
FIG. 2 shows the molecular structures of dyes used in the Examples.
Figure 2:
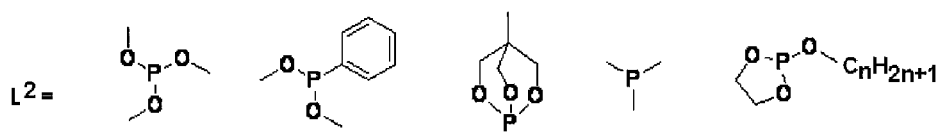

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine were added to the obtained N,N-dimethylformamide solution of trichloro(4,4',4"-tricarboxy terpyridine)ruthenium (II), five equivalents of trimethoxyphosphine were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(trimethoxyphosphine)(4,4',4"-tricarboxy terpyridine)ruthenium (II), was obtained. The structure thereof is shown in FIG. 2.

This complex was a black solid, and the measurement taken by using an electrospray mass spectrometer was 660.9, which corresponds to the molecular mass of $C_{21}H_{20}Cl_2N_3O_9PRu$.

$^1$H-NMR data were as described below.

$^1$H-NMR ($\delta$, 500 MHz), medium: (DMSO-d6), 9.44 (d, J=6 Hz, 2H), 9.05 (s, 2H), 8.90 (s, 2H), 7.93 (dd, J=2, 6 Hz, 2H), and 3.85 (d, J=10 Hz, 9H).

Figure 3:
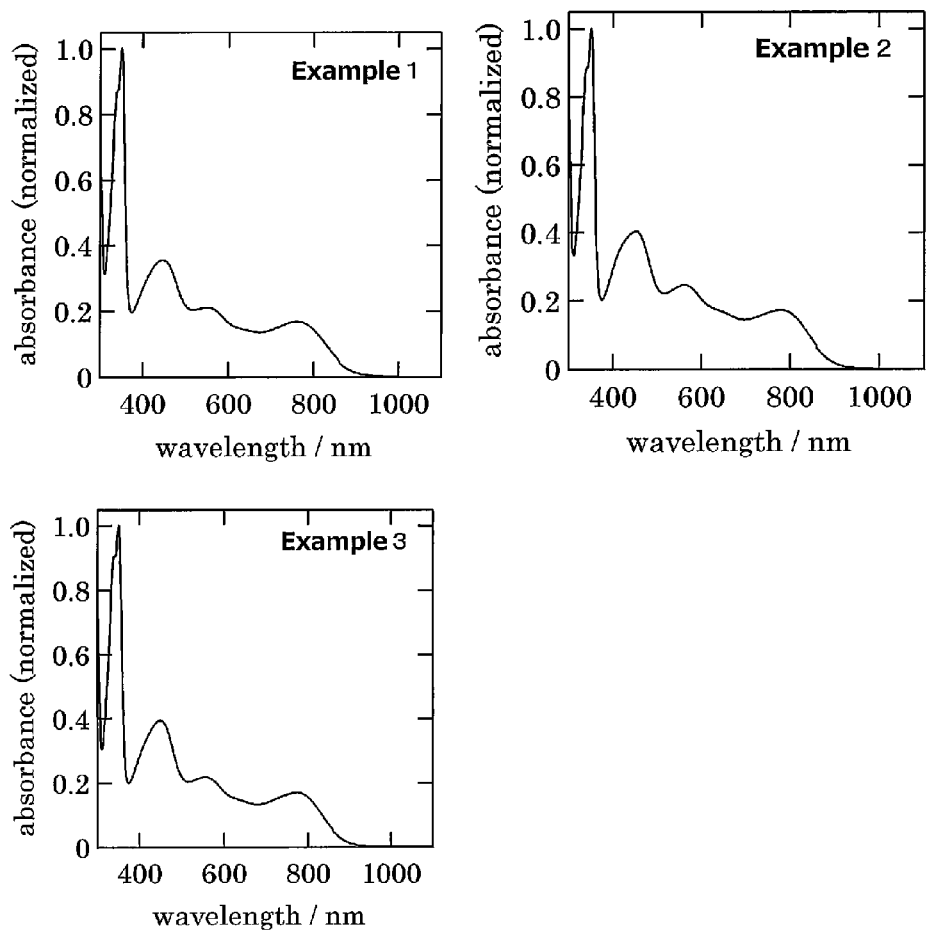
FIG. 3 shows absorption spectra of the dyes used in the Examples.

The absorption spectrum of this dye in a methanol solution is shown in FIG. 3 (Example 1).

Solar Cell Fabrication

A glass substrate having a surface resistance value of 10 Ω/sq, a size of 15 mm×25 mm, and an FTO film formed thereon was coated with titania paste Ti-Nanoxide T/SP, made by SOLARONIX SA, by means of a screen printing method and was dried at 100° C. The coated substrate was baked for 30 minutes at 450° C. When the film thickness of the baked titania semiconductor layer was measured by a contact-type thickness meter, it was 22 μm. For this substrate, an N,N-dimethylformamide solution (concentration: 0.3 μmol/L) of the dye synthesized in Example 1 was prepared, the above-described titanium oxide substrate was immersed therein for 12 hours to achieve dye adsorption, and thus, a photoelectric conversion electrode was fabricated. Himilan (film thickness 30 μm) was disposed so as to surround a counter electrode in which a Pt film having a film thickness of 1 nm was formed on a glass substrate that had two electrolyte-liquid injection holes having a diameter of 0.7 mm and that had an FTO film; the counter electrode was combined with the above-described photoelectric electrode; subsequently, an acetonitrile solution containing 0.1 mol/L lithium iodide, 0.025 mol/L iodine, and 0.6 mol/L 1-propyl-2,3-dimethylimidazolium iodide was injected through the electrolyte-liquid injection holes; and thus, a dye-sensitized solar cell having the configuration shown in FIG. 1 was fabricated.

Solar Cell Characterization

Figure 5:
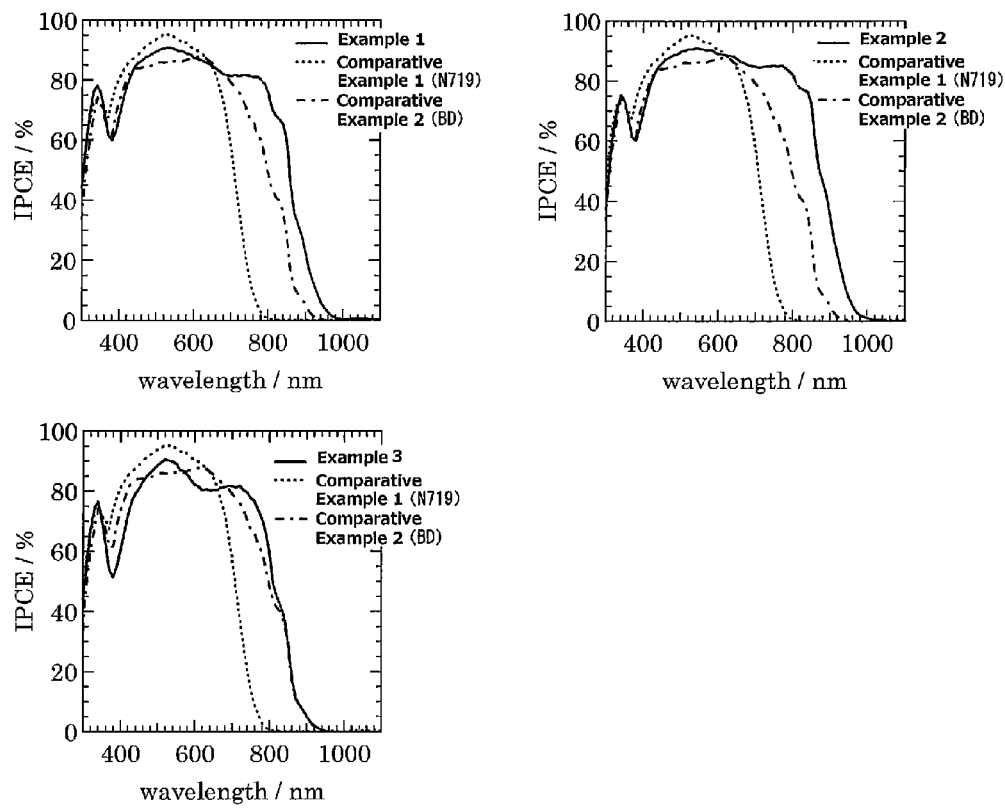
FIG. 5 shows IPCE spectra of solar cells fabricated in the Examples and Comparative Examples.

The IPCE spectrum of the cell obtained in this way was measured by using SM-250E made by Bunkoukeiki Co. Ltd. (calibrated by using a Si-PD, S1337 made by Bunkoukeiki Co. Ltd.) in a range from 300 to 1100 nm. The result is shown in FIG. 5 (Example 1). The IPCE values at 800 nm and 900 nm in the IPCE spectrum were 76% and 23%, respectively. In addition, the photoelectric conversion efficiency determined based on the current-voltage characteristic of the cell measured under simulated solar radiation (AM1.5G, 100 mW/cm$^2$: YSS-40S made by Yamashita Denso Co.) was 7.2%.

Example 2

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine were added to the obtained N,N-dimethylformamide solution of trichloro(4,4',4"-tricarboxy terpyridine)ruthenium (II), five equivalents of dimethoxyphenylphosphine were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(dimethoxyphenylphosphine)(4,4',4"-tricarboxy terpyridine)ruthenium (II), was obtained. The structure thereof is shown in FIG. 2.

This complex was a black solid, and the measurement taken by using an electrospray mass spectrometer was 707.4, which corresponds to the molecular mass of $C_{26}H_{22}Cl_2N_3O_8PRu$.

$^1$H-NMR data were as described below.

$^1$H-NMR (δ, 500 MHz), medium: (CD$_3$OD), 9.54 (d, J=6 Hz, 2H), 9.13 (s, 2H), 9.00 (s, 2H), 8.08 (t, J=5 Hz, 2H), 8.04 (dd, J=2, 6 Hz, 2H), 7.90 (d, J=5 Hz, 3H), and 4.01 (d, 10.37 Hz, 6H).

The absorption spectrum of this dye in a methanol solution is shown in FIG. 3 (Example 2).

Solar Cell Fabrication

The solar cell fabrication was performed by using the same method as in Example 1.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 5 (Example 2)). The IPCE values at 800 nm and 900 nm in the IPCE spectrum were 82% and 35%, respectively. In addition, the photoelectric conversion efficiency determined based on the current-voltage characteristic of the cell measured under simulated solar radiation (AM1.5G, 100 mW/cm$^2$: YSS-40S made by Yamashita Denso Co.) was 7.4%.

Example 3

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine are added to the obtained N,N-dimethylformamide solution of trichloro(4,4',4"-tricarboxy terpyridine)ruthenium (II), five equivalents of trimethylolpropane phosphite were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(trimethylolpropane phosphite) (4,4',4"-tricarboxy terpyridine)ruthenium (II), was obtained. The structure thereof is shown in FIG. 2.

This complex was a black solid, and the measurement taken by using an electrospray mass spectrometer was 684.9, which corresponds to the molecular mass of $C_{23}H_{20}Cl_2N_3O_9PRu$.

The absorption spectrum of the above-described dye in a methanol solution is as shown in FIG. 3 (Example 3).

Solar Cell Fabrication

The solar cell fabrication was performed by using the same method as in Example 1.

Solar-Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 5 (Example 3)). The IPCE values at 800 nm and 900 nm in the IPCE spectrum were 60% and 5%, respectively. In addition, the photoelectric conversion efficiency determined based on the current-voltage characteristic of the cell measured under simulated solar radiation (AM1.5G, 100 mW/cm$^2$: YSS-40S made by Yamashita Denso Co.) was 5.3%.

Example 4

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine were added to the obtained N,N-dimethylformamide solution of trichloro(4,4',4"-tricarboxy terpyridine)ruthenium (II), five equivalents of trimethylphosphine were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(trimethylphosphine) (4,4',4"-tricarboxy terpyridine)ruthenium (II), was obtained. The structure thereof is shown in FIG. 2.

This complex was a black solid, and the measurement taken by using an electrospray mass spectrometer was 613.3, which corresponds to the molecular mass of $C_{21}H_{20}Cl_2N_3O_6PRu$.

Figure 4:
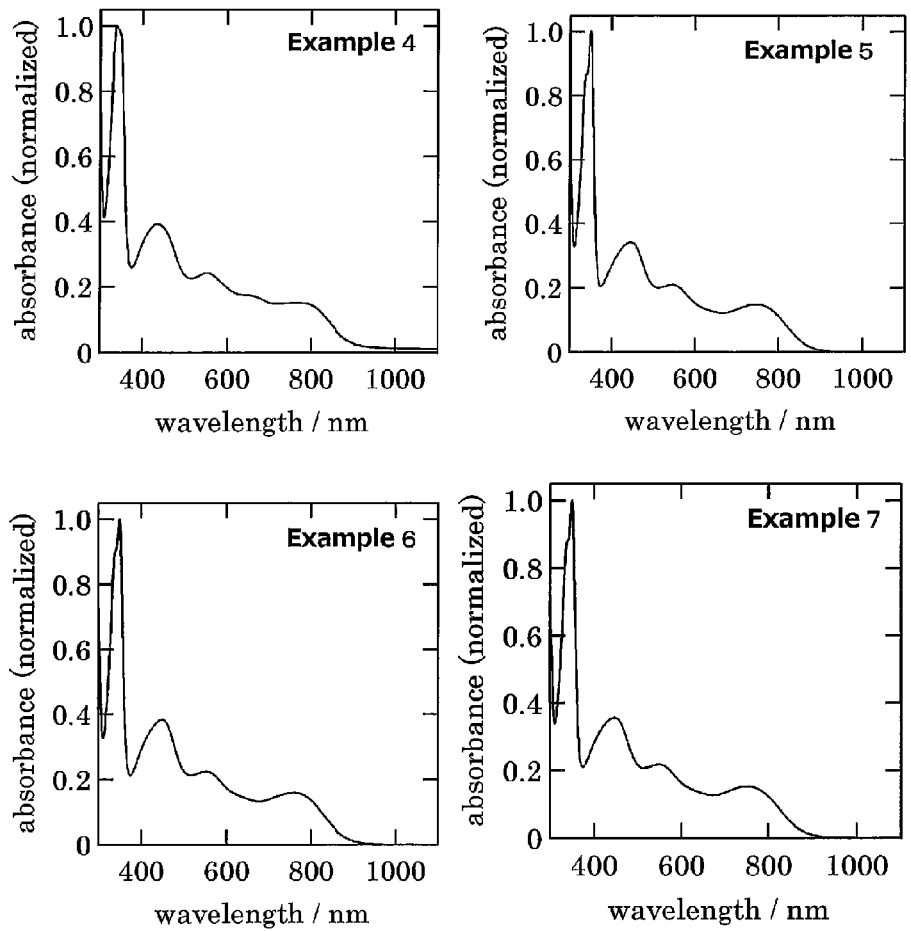
FIG. 4 shows absorption spectra of the dyes used in the Examples.

The absorption spectrum of the above-described dye in a methanol solution is as shown in FIG. 4 (Example 4).

Solar Cell Fabrication

The solar cell fabrication was performed by using the same method as in Example 1.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 6 (Example 4)). The IPCE values at 800 nm and 900 nm in the IPCE spectrum were 57% and 38%, respectively (Table 1). In addition, the photoelectric conversion efficiency determined based on the current-voltage characteristic of the cell measured under simulated solar radiation (AM1.5G, 100 mW/cm$^2$: YSS-40S made by Yamashita Denso Co.) was 2.0%.

Example 5

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine were added to the obtained N,N-dimethylformamide solution of trichloro(4,4', 4"-tricarboxy terpyridine)ruthenium (II), five equivalents of 2-methoxy-1,3,2-dioxaphospholane were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(2-methoxy-1,3,2-dioxaphospholane)(4,4',4"-tricarboxy terpyridine)ruthenium (II), was obtained. The structure thereof is shown in FIG. 2.

This complex was a black solid, and the measurement taken by using an electrospray mass spectrometer was 659.3, which corresponds to the molecular mass of $C_{21}H_{18}Cl_2N_3O_9PRu$.

The absorption spectrum of the above-described dye in a methanol solution is as shown in FIG. 4 (Example 5).

Solar Cell Fabrication

The solar cell fabrication was performed by using the same method as in Example 1.

Solar-Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 6 (Example 5)). The IPCE values at 800 nm and 900 nm in the IPCE spectrum were 68% and 10%, respectively. In addition, the photoelectric conversion efficiency determined based on the current-voltage characteristic of the cell measured under simulated solar radiation was 7.7% (Table 1). The photoelectric conversion efficiency determined based on the current-voltage characteristic of the cell measured under simulated solar radiation (AM1.5G, 100 mW/cm$^2$: YSS-40S made by Yamashita Denso Co.) was 7.7%.

Example 6

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine were added to the obtained N,N-dimethylformamide solution of trichloro(4,4',4"-tricarboxy terpyridine)ruthenium (II), five equivalents of 2-octyloxy-1,3,2-dioxaphospholane were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(2-octyloxy-1,3,2-dioxaphospholane) (4,4',4"-tricarboxy terpyridine)ruthenium (II), was obtained. The structure thereof is shown in FIG. 2.

This complex was a black solid, and the measurement taken by using an electrospray mass spectrometer was 757.0, which corresponds to the molecular mass of $C_{28}H_{32}Cl_2N_3O_9PRu$.

The absorption spectrum of the above-described dye in a methanol solution is as shown in FIG. 4 (Example 6).

Solar Cell Fabrication

The solar cell fabrication was performed by using the same method as in Example 1.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 6 (Example 6)). The IPCE values at 800 nm and 900 nm in the IPCE spectrum were 67% and 13%, respectively. The photoelectric conversion efficiency determined based on the current-voltage characteristic of the cell measured under simulated solar radiation (AM1.5G, 100 mW/cm$^2$: YSS-40S made by Yamashita Denso Co.) was 7.1%.

Example 7

Dye Synthesis 4,4',4"-tricarboxy terpyridine and ruthenium trichloride were subjected to thermal reflux for 3 hours in ethanol under an argon atmosphere. After cooling, the medium was removed by means of distillation by using a rotary evaporator, two equivalents of ethylenediamine were added to the obtained N,N-dimethylformamide solution of trichloro(4,4',4"-tricarboxy terpyridine)ruthenium (II), five equivalents of 2-cetyloxy-1,3,2-dioxaphospholane were additionally added thereto, and the solution was heated for five minutes at 70° C. The reaction mixture was cooled to room temperature and, after adding trifluoroacetic acid, was agitated for five minutes; the medium was subsequently removed by means of distillation by using a rotary evaporator; and, after adding diethyl ether thereto, the residue was left to stand overnight at 0° C. By separating the solid product by means of filtering, the desired complex, i.e., dichloro(2-cetyloxy-1,3,2-dioxaphospholane)(4,4',4"-tricarboxy terpyridine)ruthenium (II), was obtained. The structure thereof is shown in FIG. 2.

This complex was a black solid, and the measurement taken by using an electrospray mass spectrometer was 869.1, which corresponds to the molecular mass of $C_{36}H_{48}Cl_2N_3O_9PRu$.

The absorption spectrum of the above-described dye in a methanol solution is as shown in FIG. 4 (Example 7).

Solar Cell Fabrication

The solar cell fabrication was perfoLmed by using the same method as in Example 1.

Solar-Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 6 (Example 7)). The IPCE values at 800 nm and 900 nm in the IPCE spectrum were 68% and 13%, respectively. The photoelectric conversion efficiency determined based on the current-voltage characteristic of the cell measured under simulated solar radiation (AM1.5G, 100 mW/cm$^2$: YSS-40S made by Yamashita Denso Co.) was 7.5%.

Example 8

Dye synthesis

The dye synthesis was performed by using the same method as in Example 1.

Solar Cell Fabrication

A glass substrate having a surface resistance value of 10 Ω/sq, a size of 15 mm×25 mm, and an FTO film formed thereon was coated with titania paste Ti-Nanoxide T/SP, made by SOLARONIX SA, by means of a screen printing method and was dried at 100° C. The coated substrate was baked for 30 minutes at 450° C. When the film thickness of the baked titania semiconductor layer was measured by a contact-type thickness meter, it was 22 μm. For this substrate, an N,N-dimethylformamide solution (concentration: 0.3 μmol/L) of the above-described dye was prepared, the above-described titanium oxide substrate was immersed therein for 12 hours to achieve dye adsorption, and thus, a photoelectric conversion electrode was fabricated. Himilan (film thickness 30 μm) was disposed so as to surround a counter electrode in which a Pt film having a film thickness of 1 nm was formed on a glass substrate that had two electrolyte-liquid injection holes having diameter of 0.7 mm and that had an FTO film; the counter electrode was combined with the above-described photoelectric electrode; subsequently, an acetonitrile solution containing 0.1 mol/L lithium iodide, 0.025 mol/L iodine, 0.6 mol/L 1-propyl-2,3-dimethylimidazolium iodide, and 0.2 mol/L 4-t-butylpyridine was injected through the electrolyte-liquid injection holes; and thus, a dye-sensitized solar cell having the same configuration as that in FIG. 1 was fabricated.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 7 (Example 8)). The IPCE values at 800 nm and 900 nm in the IPCE spectrum were 61% and 14%, respectively. The photoelectric conversion efficiency determined based on the current-voltage characteristic of the cell measured under simulated solar radiation (AM1.5G, 100 mW/cm$^2$: YSS-40S made by Yamashita Denso Co.) was 9.0%.

Example 9

Dye Synthesis

The dye synthesis was performed by using the same method as in Example 2.

Solar Cell Fabrication

The solar cell fabrication was performed by using the same method as in Example 8.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm (FIG. 7 (Example 9)). The IPCE values at 800 nm and 900 nm in the IPCE spectrum were 58% and 10%, respectively. The photoelectric conversion efficiency determined based on the current-voltage characteristic of the cell measured under simulated solar radiation (AM1.5G, 100 mW/cm$^2$: YSS-40S made by Yamashita Denso Co.) was 9.9%.

Comparative Example 1

Solar Cell Fabrication

A glass substrate having a surface resistance value of 10 Ω/sq, a size of 15 mm×25 mm, and an FTO film formed thereon was coated with titania paste Ti-Nanoxide T/SP, made by SOLARONIX SA, by means of a screen printing method and was dried at 100° C. The coated substrate was baked for 30 minutes at 450° C. When the film thickness of the baked titania semiconductor layer was measured by a contact-type thickness meter, it was 22 μm. For this substrate, an N,N-dimethylformamide solution (concentration: 0.3 μmol/L) of a ruthenium complex derivative (N719, made by SOLARONIX SA) was prepared, the above-described titanium oxide substrate was immersed therein for 12 hours to achieve dye adsorption, and thus, a photoelectric conversion electrode was fabricated. Himilan (film thickness 30 μm) was disposed so as to surround a counter electrode in which a Pt film having a film thickness of 1 nm was formed on a glass substrate that had two electrolyte-liquid injection holes having diameter of 0.7 mm and that had an FTO film; the counter electrode was combined with the above-described photoelectric electrode; subsequently, an acetonitrile solution containing 0.1 mol/L lithium iodide, 0.025 mol/L iodine, and 0.6 mol/L 1-propyl-2,3-dimethylimidazolium iodide was injected through the electrolyte-liquid injection holes; and thus, a dye-sensitized solar cell having the same configuration as that in FIG. 1 was fabricated.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm. The IPCE values at 800 nm and 900 nm in the IPCE spectrum were 0.79% and 0.09%, respectively, which were values that can be regarded as noise levels in the measurement. The photoelectric conversion efficiency determined based on the current-voltage characteristic of the cell measured under simulated solar radiation (AM1.5G, 100 mW/cm$^2$: YSS-40S made by Yamashita Denso Co.) was 8.2%.

Comparative Example 2

Solar Cell Fabrication

A glass substrate having a surface resistance value of 10 Ω/sq, a size of 15 mm×25 mm, and an FTO film formed thereon was coated with titania paste Ti-Nanoxide T/SP, made by SOLARONIX SA, by means of a screen printing method and was dried at 100° C. The coated substrate was baked for 30 minutes at 450° C. When the film thickness of the baked titania semiconductor layer was measured by a contact-type thickness meter, it was 22 μm. For this substrate, an N,N-dimethylformamide solution (concentration: 0.3 μmol/L) of a ruthenium complex derivative (Black Dye (BD), made by SOLARONIX SA) was prepared, the above-described titanium oxide substrate was immersed therein for 12 hours to achieve dye adsorption, and thus, a photoelectric conversion electrode was fabricated. Himilan (film thickness 30 μm) was disposed so as to surround a counter electrode in which a Pt film having a film thickness of 1 nm was formed on a glass substrate that had two electrolyte-liquid injection holes having diameter of 0.7 mm and that had an FTO film; the counter electrode was combined with the above-described photoelectric electrode; subsequently, an acetonitrile solution containing 0.1 mol/L lithium iodide, 0.025 mol/L iodine, and 0.6 mol/L 1-propyl-2,3-dimethylimidazolium iodide was injected through the electrolyte-liquid injection holes; and thus, a dye-sensitized solar cell having the same configuration as that in FIG. 1 was fabricated.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm. The IPCE values at 800 nm and 900 nm in the IPCE spectrum were 49% and 5%, respectively. The photoelectric conversion efficiency determined based on the current-voltage characteristic of the cell measured under simulated solar radiation (AM1.5G, 100 mW/cm$^2$: YSS-40S made by Yamashita Denso Co.) was 7.0%.

Comparative Example 3

Solar Cell Fabrication

A glass substrate having a surface resistance value of 10 Ω/sq, a size of 15 mm×25 mm, and an FTO film formed thereon was coated with titania paste Ti-Nanoxide T/SP, made by SOLARONIX SA, by means of a screen printing method and was dried at 100° C. The coated substrate was baked for 30 minutes at 450° C. When the film thickness of the baked titania semiconductor layer was measured by a contact-type thickness meter, it was 22 μm. For this substrate, an N,N-dimethylformamide solution (concentration: 0.3 μmol/L) of a [ruthenium complex derivative (N719, made by SOLARONIX SA) was prepared, the above-described titanium oxide substrate was immersed therein for 12 hours to achieve dye adsorption, and thus, a photoelectric conversion electrode was fabricated. Himilan (film thickness 30 μm) was disposed so as to surround a counter electrode in which a Pt film having a film thickness of 1 nm was formed on a glass substrate that had two electrolyte-liquid injection holes having diameter of 0.7 mm and that had an FTO film; the counter electrode was combined with the above-described photoelectric electrode; subsequently, an acetonitrile solution containing 0.1 mol/L lithium iodide, 0.025 mol/L iodine, 0.6 mol/L 1-propyl-2,3-dimethylimidazolium iodide, and 0.5 mol/L 4-t-butylpyridine was injected through the electrolyte-liquid injection holes; and thus, a dye-sensitized solar cell having the same configuration as that in FIG. 1 was fabricated.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm. The IPCE value at 800 nm in the IPCE spectrum was 3%. The photoelectric conversion efficiency determined based on the current-voltage characteristic of the cell measured under simulated solar radiation (AM1.5G, 100 mW/cm$^2$: YSS-405 made by Yamashita Denso Co.) was 9.8%.

Comparative Example 4

Solar Cell Fabrication

A glass substrate having a surface resistance value of 10 Ω/sq, a size of 15 mm×25 mm, and an FTO film formed thereon was coated with titania paste Ti-Nanoxide T/SP, made by SOLARONIX SA, by means of a screen printing method and was dried at 100° C. The coated substrate was baked for 30 minutes at 450° C. When the film thickness of the baked titania semiconductor layer was measured by a contact-type thickness meter, it was 22 μm. For this substrate, an N,N-dimethylformamide solution (concentration: 0.3 μmol/L) of a ruthenium complex derivative (Black Dye (BD), made by SOLARONIX SA) was prepared, the above-described titanium oxide substrate was immersed therein for 12 hours to achieve dye adsorption, and thus, a photoelectric conversion electrode was fabricated. Himilan (film thickness 30 μm) was disposed so as to surround a counter electrode in which a Pt film having a film thickness of 1 nm was formed on a glass substrate that had two electrolyte-liquid injection holes having diameter of 0.7 mm and that had an FTO film; the counter electrode was combined with the above-described photoelectric electrode; subsequently, an acetonitrile solution containing 0.1 mol/L lithium iodide, 0.025 mol/L iodine, 0.6 mol/L 1-propyl-2,3-dimethylimidazolium iodide, and 0.5 mol/L 4-t-butylpyridine was injected through the electrolyte-liquid injection holes; and thus, a dye-sensitized solar cell having the same configuration as that in FIG. 1 was fabricated.

Solar Cell Characterization

The IPCE spectrum of the cell fabricated by using the method described above was measured by using SM-250E made by Bunkoukeiki Co. Ltd. (calibrated by using a Si-PD, S1337 made by Bunkoukeiki Co. Ltd.) in a range from 300 to 1100 nm. The IPCE values at 800 nm and 900 nm in the IPCE spectrum were 34% and 3%, respectively. The photoelectric conversion efficiency determined based on the current-voltage characteristic of the cell measured under simulated solar radiation (AM1.5G, 100 mW/cm$^2$: YSS-40S made by Yamashita Denso Co.) was 9.0%.

Figure 6:
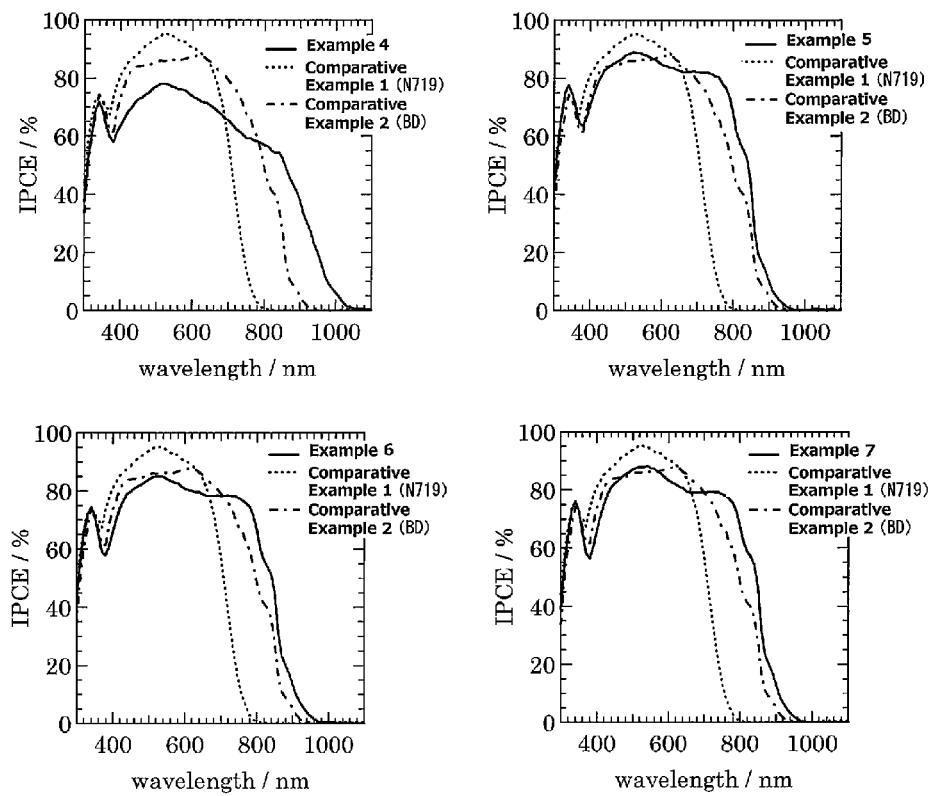
FIG. 6 shows IPCE spectra of solar cells fabricated in the Examples and Comparative Examples.
Figure 7:
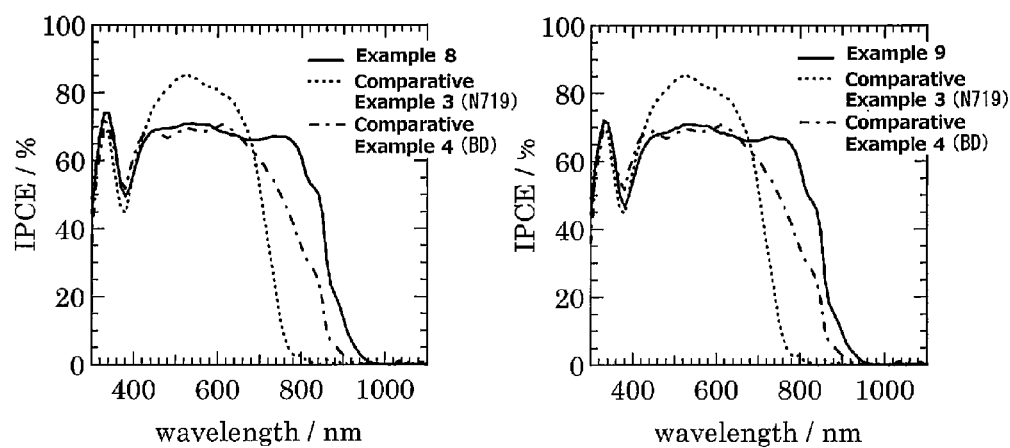
FIG. 7 shows IPCE spectra of solar cells fabricated in the Examples and Comparative Examples.

Note that the results for Comparative Examples 1 and 2 are shown in FIGS. 5 and 6 together with the results for Examples 1 to 7, and the results for Comparative Examples 3 and 4 are shown in FIG. 7 together with the results for Examples 8 and 9.

The results described above are summarized in the table below.

TABLE 1

The solar cell characterization of the solar cells fabricated in Examples and Comparative Examples.

| | Dye | TBP*[1] | Voc/V | Jsc/mAcm$^{-2}$ | FF | η/% |
|---|---|---|---|---|---|---|
| Example 1 | Example 1 | — | 0.54 | 25.1 | 0.54 | 7.2 |
| Example 2 | Example 2 | — | 0.52 | 26.8 | 0.53 | 7.4 |
| Example 3 | Example 3 | — | 0.48 | 22.9 | 0.49 | 5.3 |
| Example 4 | Example 4 | — | 0.39 | 19.4 | 0.27 | 2 |
| Example 5 | Example 5 | — | 0.53 | 23.6 | 0.61 | 7.7 |
| Example 6 | Example 6 | — | 0.51 | 23.8 | 0.59 | 7.1 |
| Example 7 | Example 7 | — | 0.51 | 24.5 | 0.59 | 7.5 |
| Example 8 | Example 1 | 0.2 | 0.65 | 21.7 | 0.64 | 9 |
| Example 9 | Example 2 | 0.2 | 0.66 | 21.4 | 0.7 | 9.9 |
| Comparative Example 1 | N719 | — | 0.63 | 20.5 | 0.63 | 8.2 |
| Comparative Example 2 | Black Dye | — | 0.52 | 23.1 | 0.58 | 7 |
| Comparative Example 3 | N719 | 0.5 | 0.75 | 18 | 0.72 | 9.8 |
| Comparative Example 4 | Black Dye | 0.5 | 0.67 | 20.5 | 0.65 | 9 |

*[1] means the amount to be added of 4-t-butylpyridine in the electrolyte.

Example 10

Solar Cell Fabrication

Two glass substrates (referred to as substrates A and B) having surface resistance values of 10 Ω/sq, sizes of 15 mm×25 mm, and FTO films formed thereon were coated with titania paste Ti-Nanoxide T/SP, by SOLARONIX SA, by means of a screen printing method so that thicknesses thereof differ between the substrate A and the substrate B, and the substrates were dried at 100° C.

The coated substrates were baked for 30 minutes at 450° C. When the film thicknesses of the baked titania semiconductor layers were measured by a contact-type thickness meter, they were 5 μm and 19 μm for the substrate A. For the substrate A, a mixed solution of acetonitrile and t-butyl alcohol (concentration: 0.3 μmol/L) of a ruthenium complex derivative (N719, made by SOLARONIX SA) was prepared, the above-described titanium oxide substrate A was immersed therein for 20 hours to achieve dye adsorption, and thus, a photoelectric conversion electrode A was fabricated.

An N,N-dimethylformamide solution (concentration: 0.3 μmol/L) of the ruthenium complex derivative fabricated in Example 2 was prepared, the above-described titanium oxide substrate B was immersed therein for 12 hours to achieve dye adsorption, and thus, a photoelectric conversion electrode B was fabricated.

Himilan (film thickness 30 μm) was disposed so as to surround a transparent counter electrode in which a Pt film was formed on a glass substrate that had an FTO film; the transparent counter electrode was combined with the above-described photoelectric electrode A; subsequently, an acetonitrile solution containing 0.1 mol/L lithium iodide, 0.025 mol/L iodine, 0.6 mol/L 1-propyl-2,3-dimethylimidazolium iodide, and 0.5 mol/L 4-t-butylpyridine was injected; and thus, a dye-sensitized solar cell A having the same configuration as that in FIG. 1 was fabricated.

Himilan (film thickness 30 μm) was disposed so as to surround a transparent counter electrode in which a Pt film was formed on a glass substrate that had an FTO film; the transparent counter electrode was combined with the above-described photoelectric electrode B; subsequently, an acetonitrile solution containing 0.1 mol/L lithium iodide, 0.025 mol/L iodine, 0.6 mol/L 1-propyl-2,3-dimethylimidazolium iodide, and 0.1 mol/L 4-t-butylpyridine was injected; and thus, a dye-sensitized solar cell having the same configuration as that in FIG. 1 was fabricated.

The dye-sensitized solar cell A was placed on the dye-sensitized solar cell B so that the positions of the titanium oxide semiconductor layers were aligned, thereby connecting the two solar-cell cells in series, and thus, a tandem-type dye-sensitized solar cell was fabricated.

Solar Cell Characterization

Measurements were taken by using the same method as in Example 1.

Figure 8:
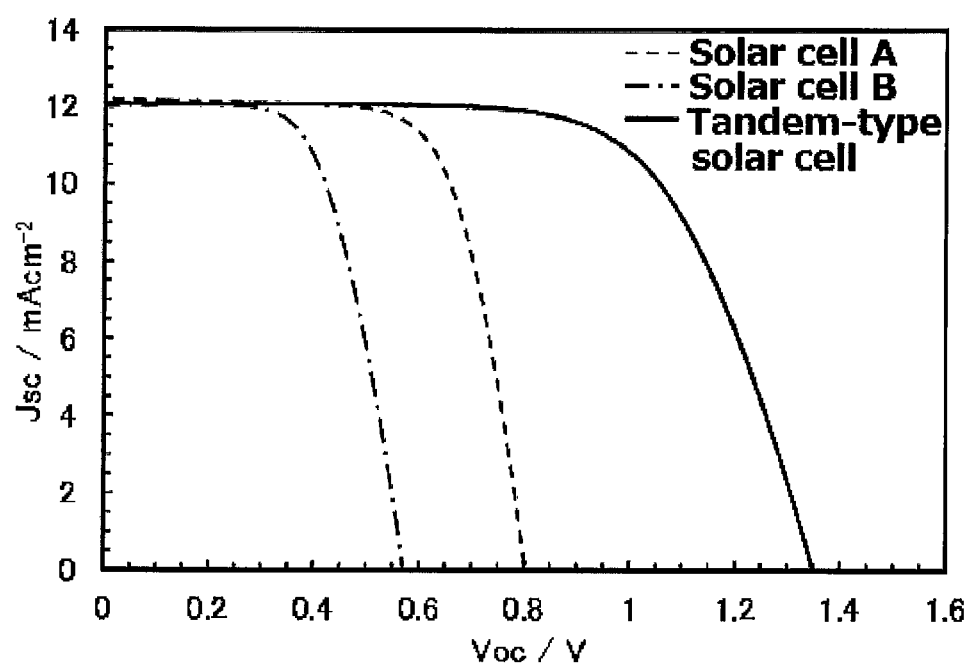
FIG. 8 is a graph showing the current-voltage characteristic of a tandem-type solar cell fabricated in an Example.

The respective current-voltage characteristics of the solar-cell cell A portion, the solar-cell cell B portion, and the unit in which they are connected in series (tandem-type solar cell) were measured. When taking these measurements, in order to limit the area irradiated with light, the surface of the cell on the side irradiated with light was covered with a mask that blocked light except for a 5-mm square opening. Note that light was radiated from the solar cell A side. A graph showing the current-voltage characteristics is shown in FIG. 8.

In addition, the measurements results of current-voltage characteristics described above are summarized in Table 2 below.

TABLE 2

The solar cell characterization of the tandem-type solar cell

| Dye | | Voc/V | Jsc/mAcm$^{-2}$ | FF | η/% |
|---|---|---|---|---|---|
| Solar cell A | N719 | 0.8 | 12.2 | 0.7 | 6.8 |
| Solar cell B | Example 2 | 0.57 | 12.1 | 0.57 | 4.3 |

TABLE 2-continued

The solar cell characterization of the tandem-type solar cell

| Dye | | Voc/V | Jsc/mAcm$^{-2}$ | FF | η/% |
|---|---|---|---|---|---|
| Tandem-type solar cell | N719 + Example 2 | 1.35 | 12.1 | 0.66 | 10.8 |

Explanation Of Reference:
1: light-transmitting conductive substrate
2: photoelectric conversion film
3: counter electrode
4: electrolyte layer
5: sealing material

The invention claimed is:

1. A photoelectric-conversion-device dye comprising:
a ruthenium metal complex, which includes a molecule including elemental phosphorus and the molecule forms a coordinate bond at least at the phosphorus atom, and which also includes a terpyridine derivative that forms a coordinate bond and has at least one adsorbing group that exhibits adsorptivity toward a metal oxide
wherein the at least one adsorbing group is selected from the group consisting of a carboxylic acid group, an ester thereof, or a salt thereof; a phosphonic acid group, an ester thereof, or a salt thereof; a hydroxy group; an alkoxy group; and a sulfonic acid group or salt thereof.

2. A photoelectric-conversion-device dye according to claim 1, wherein the metal complex is a metal complex that exhibits absorption due to a spin-forbidden transition.

3. A photoelectric-conversion-device dye according to claim 1, wherein the metal complex is represented by (I) below:

[Ruthenium($L^1$)($L^2$)($L^3$)$_{3-n}$]   (I)

where $L^1$ represents a terpyridine derivative represented by (L1) below; $L^2$ represents an organic molecule including elemental phosphorous, represented by (L2) below; $L^3$ represents a halogen atom, NCS$^-$, SCN$^-$, CN or NCO$^-$; and n is an integer of 1 to 3;

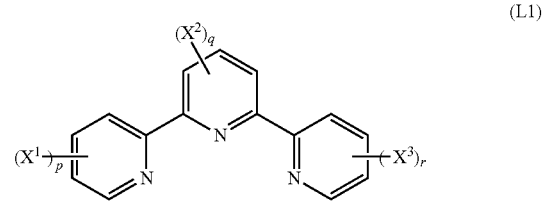

(L1)

where $X^1$ to $X^3$ represent adsorbing groups that are the same as or different from each other and have adsorptivity toward a metal oxide; and p, q, and r are each an integer of 0 to 5, wherein at least one of them is equal to or greater than 1; and

P($R^1$)($R^2$)($R^3$)   (L2)

where $R^1$ to $R^3$ each represent an alkyl group, an alkenyl group, an aryl group, an alkyloxy group, or an aryloxy group that are the same as or different from each other; $R^1$ to $R^3$ may have a substituent; and $R^1$ to $R^3$ may also be bonded with each other to form one or more rings.

4. A photoelectric-conversion-device dye according to claim 1, wherein the adsorbing group is a carboxylic acid group (—COOH), a salt thereof, or an ester thereof.

5. A photoelectric-conversion-device dye according to claim 3, wherein $L^2$ is an organic molecule including elemental phosphorous, represented by (L2-1) or (L2-2) below:

$$P(OR^{11})_m(R^{12})_{3-m} \tag{L2-1}$$

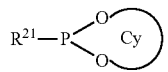
(L2-2)

wherein $R^{11}$ and $R^{12}$ each represent an alkyl group or an aryl group, which may include substitution; m is an integer of 0 to 3; when a plurality of $OR^{11}$ and $R^{12}$ are included, they may be the same as or different from each other; Cy represents a ring group having one phosphorous atom and two oxygen atoms as constituent atoms of the ring; Cy may have a substituent; Cy may also take a condensed form including one or more rings; $R^{21}$ represents an alkyl group, an aryl group, an alkyloxy group, or an aryloxy group; $R^{21}$ may have a substituent; and $R^{21}$ may form a ring by bonding with a constituent atom of the ring in Cy.

6. A photoelectric-conversion-device dye according to claim 3, wherein n is 1.

7. A photoelectric conversion film at least comprising:
a photoelectric-conversion-device dye according to claim 1; and
a metal oxide semiconductor.

8. An electrode comprising:
a photoelectric conversion film according to claim 7.

9. A solar cell at least comprising:
an electrode according to claim 8;
a counter electrode therefor; and
an electrolyte layer that is disposed therebetween.

10. A solar cell according to claim 9, wherein the electrolyte layer contains at least a pyridine derivative.

11. A tandem-type solar cell at least comprising:
a solar cell according to claim 9.

12. A photoelectric-conversion-device dye according to claim 2, wherein the metal complex is represented by (I) below:

$$[\text{Ruthenium}(L^1)(L^2)_n(L^3)_{3-n}] \tag{I}$$

where $L^1$ represents a terpyridine derivative represented by (L1) below; $L^2$ represents an organic molecule including elemental phosphorous, represented by (L2) below; $L^3$ represents a halogen atom, $NCS^-$, $SCN^-$, $CN$ or $NCO^-$; and n is an integer of 1 to 3;

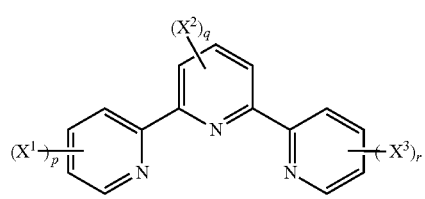
(L1)

where $X^1$ to $X^3$ represent adsorbing groups that are the same as or different from each other and have adsorptivity toward a metal oxide; and p, q, and r are each an integer of 0 to 5, wherein at least one of them is equal to or greater than 1; and $$P(R^1)(R^2)(R^3) \tag{L2}$$

where $R^1$ to $R^3$ each represent an alkyl group, an alkenyl group, an aryl group, an alkyloxy group, or an aryloxy group that are the same as or different from each other; $R^1$ to $R^3$ may have a substituent; and $R^1$ to $R^3$ may also be bonded with each other to form one or more rings.

13. A photoelectric-conversion-device dye according to claim 2, wherein the adsorbing group is a carboxylic acid group (—COOH), a salt thereof, or an ester thereof.

14. A photoelectric-conversion-device dye according to claim 3, wherein the adsorbing group is a carboxylic acid group (—COOH), a salt thereof, or an ester thereof.

15. A photoelectric-conversion-device dye according to claim 12, wherein $L^2$ is an organic molecule including elemental phosphorous, represented by (L2-1) or (L2-2) below:

$$P(OR^{11})_m(R^{12})_{3-m} \tag{L2-1}$$

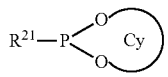
(L2-2)

wherein $R^{11}$ and $R^{12}$ each represent an alkyl group or an aryl group, which may include substitution; m is an integer of 0 to 3; when a plurality of $OR^{11}$ and $R^{12}$ are included, they may be the same as or different from each other; Cy represents a ring group having one phosphorous atom and two oxygen atoms as constituent atoms of the ring; Cy may have a substituent; Cy may also take a condensed form including one or more rings; $R^{21}$ represents an alkyl group, an aryl group, an alkyloxy group, or an aryloxy group; $R^{21}$ may have a substituent; and $R^{21}$ may form a ring by bonding with a constituent atom of the ring in Cy.

16. A photoelectric-conversion-device dye according to claim 5, wherein n is 1.

17. A photoelectric conversion film at least comprising:
a photoelectric-conversion-device dye according to claim 2 and
a metal oxide semiconductor.

* * * * *

UNITED STATES PATENT AND TRADEMARK OFFICE
CERTIFICATE OF CORRECTION

| | |
|---|---|
| PATENT NO. | : 8,941,008 B2 |
| APPLICATION NO. | : 14/003056 |
| DATED | : January 27, 2015 |
| INVENTOR(S) | : H. Segawa et al. |

It is certified that error appears in the above-identified patent and that said Letters Patent is hereby corrected as shown below:

Claims

At column 25, line 29 (i.e., the third line of claim 7) of the printed patent, delete ";" after 1.

Signed and Sealed this
Seventeenth Day of November, 2015

Michelle K. Lee
*Director of the United States Patent and Trademark Office*